United States Patent [19]
Hillman et al.

[11] Patent Number: 5,998,372
[45] Date of Patent: Dec. 7, 1999

[54] ZINC RING PROTEIN

[75] Inventors: Jennifer L. Hillman, Mountain View; Preeti Lal; Purvi Shah, both of Sunnyvale, all of Calif.

[73] Assignee: Incyte Pharmaceuticals, Inc., Palo Alto, Calif.

[21] Appl. No.: 09/128,369

[22] Filed: Aug. 3, 1998

Related U.S. Application Data

[62] Division of application No. 08/867,057, Jun. 2, 1997, Pat. No. 5,840,555.
[51] Int. Cl.$^6$ .......................... A61K 38/00; A61K 38/16; C07K 1/00
[52] U.S. Cl. .............................. 514/12; 530/350; 530/358
[58] Field of Search ..................................... 530/350, 358; 514/12

[56] References Cited

PUBLICATIONS

Berg, J.M. et al., "The Galvanization of Biology: A Growing Appreciation for the Roles of Zinc", *Science*, 271: 1081–1085 (1996).

Lovering, R. et al., "Identification and preliminary characterization of a protein motif related to the zinc finger", *Proc. Natl. Acad. Sci.*, 90: 2112–2116 (1993).

Barlow, P.N. et al., "Structure of the $C_3HC_4$ Domain by $^1$H–nuclear Magnetic Resonance Spectroscopy. A New Structual Class of Zinc–finger", *J. Mol. Biol.*, 237: 201–211 (1994).

Haupt, Y. et al., "Novel Zinc Finger Gene Implicated as myc Collaborator by Retrovirally Accelerated Lymphomagenesis in Eμ–myc Transgenic Mice", *Cell*, 65:753–763 (1991).

Alkema, M.J. et al., "Characterization and chromosomal localization of the human proto–oncogene BMI–1", *Hum. Mol. Genet.*, 2: 1597–1603 (1993).

Miki, Y. et al., "A Strong Candidate for the Breast and Ovarian Cancer Susceptibility Gene BRCA1 ", *Science*, 266:66–71 (1994).

Thompson, M.E. et al., "Decreased expression of BRCA1 accelerates growth and is often present during sporadic breast cancer progression", *Nature Genet.*, 9: 444–450 (1995).

Tranque, P. et al., "Identification and characterization of a RING Zinc finger gene (C–RZF) expressed in chicken embryo cells", *Proc. Natl. Acad. Sci.*, 93: 3105–3109 (1996) (GI 1321818).

Zamore, P.D. et al., "Cloning and domain structure of the mammalian splicing factor U2AF", *Nature*, 355: 609–614 (1992).

Hillier, L. et al., (Direct Submission), GenBank Sequence Database (Accession T80259), National Center for Biotechnology Information, National Library of Medicine, Bethesda, Maryland, 20894 (GI 698769), Mar. 8, 1995.

Hillier, L. et al., (Direct Submission), GenBank Sequence Database (Accession N32697), National Center for Biotechnology Information, National Library of Medicine, Bethesda, Maryland, 20894 (GI 1153096), Jan. 10, 1996.

Hillier, L. et al., "The WashU–Merck Project," EMBL Database, Accession No. W00513, Heidelberg, Germany, Apr. 19, 1996.

Lomax, M. et al, "The gene for a RING zinc finger protein is expressed in the inner ear," EMBL Database, Accession No. AF037204, Heidelberg, Germany, Jan. 9, 1998.

Tranque et al., Proc. Natl. acad. Sci. USA, 93, 3105–3109, Apr. 1996.

*Primary Examiner*—Robert A. Wax
*Assistant Examiner*—Maryam Monshipouri
*Attorney, Agent, or Firm*—Incyte Pharmaceuticals, Inc.; Sheela Mohan-Peterson

[57] ABSTRACT

The invention provides a human zinc RING protein (ZIRI) and polynucleotides which identify and encode ZIRI. The invention also provides expression vectors, host cells, agonists, antibodies and antagonists. The invention also provides methods for treating disorders associated with expression of ZIRI.

2 Claims, 8 Drawing Sheets

```
5' GTT GTC GTC CCT GCT AGT ACT CCG GGC TGT GGG GGT CGG GGA TAT TCA GTC    54
                                   9        18           27           36           45

ATG AAA TCA GGG TAG GGA CTT CTC CCG CAG CGA CGC GGC TGG CAA GAC TGT TTG   108
                                   63          72          81          90          99

TGT TGC GGG GGC CGG ACT TCA AGG TGA TTT TAC AAC GAG ATG CTG CTC TCC ATA   162
                                  117         126         135        144         153        I
                                                                              M   L   L   S

GGG ATG CTC ATG CTG TCA GCC ACA CAA GTC TAC ACC ATC TTG ACT GTC CAG CTC   216
 G   M   L   M   L   S   A   T   Q   V   Y   T   I   L   T   V   Q   L
                                  171         180         189         198         207

TTT GCA TTC TTA AAC CTA CTG CCT GTA GAA GCA GAC CTC CCT GCA AGA TTT TTT   270
 F   A   F   L   N   L   L   P   V   E   A   D   L   P   A   R   F   F
                                  225         234         243         252         261

GAA AAT GCA TCT CAG GGT TTT GAT GAC TTT GGT TAT AGA CTT         324
 E   N   A   S   Q   G   F   D   D   F   G   Y   R   L
                                  279         288         297         306         315

CCA GCT GAA GGT TTA AAG GGT TTG ATT AAC TCA AAA CCA GAG AAT GCC TGT       378
 P   A   E   G   L   K   G   F   L   I   N   S   K   P   E   N   A   C
                                  333         342         351         360         369
```

FIGURE 1A

```
     387           396           405           414           423           432
GAA CCC ATA GTG   CCT CCA GTA   AAT GAC AAA   TCA TCT GGC   ACT TTC ATC GTG
 E   P   I   V     P   P   V     N   D   K     S   S   G     T   F   I   V
     441           450           459           468           477           486
TTA ATT AGA AGA   CTT GAT TGT   AAT TTT GAT   ATA AAG GTT   TTA AAT GCA CAG AGA
 L   I   R   R     L   D   C     N   F   D     I   K   V     L   N   A   Q   R
     495           504           513           522           531           540
GCA GGA TAC AAG   GCA GCC ATA   GTT CAC AAT   GTT GAT TCT   GAT CTC ATT AGC
 A   G   Y   K     A   A   I     V   H   N     V   D   S     D   L   I   S
     549           558           567           576           585           594
ATG GGA TCC AAC   GAC ATT GAG   GTA CTA AAG   AAA ATT GAC   ATT CCA TCT GTC TTT
 M   G   S   N     D   I   E     V   L   K     K   I   D     I   P   S   V   F
     603           612           621           630           639           648
ATT GGT GAA TCA   TCA GCT AAT   TCT CTG AAA   GAT GAA TTC   ACA TAT GAA AAA GGG
 I   G   E   S     S   A   N     S   L   K     D   E   F     T   Y   E   K   G
     657           666           675           684           693           702
GGC CAC CTT ATC   TTA GTT CCA   GAA TTT AGT   CTT CCT TTG   GAA TAC TAC CTA ATT
 G   H   L   I     L   V   P     E   F   S     L   P   L     E   Y   Y   L   I
     711           720           729           738           747           756
CCC TTC CTT ATC   ATA GTG GGC   ATC TTG TGT   CTC ATC TTG   ATA GTC ATT TTC ATG ATC
 P   F   L   I     I   V   G     I   L   C     L   I   L     I   V   I   F   M   I
```

FIGURE 1B

```
      765            774            783            792            801            810
ACA AAA TTT GTC CAG GAT AGA CAT AGA GCT AGA AAC AGA CTT CGT AAA GAT
 T   K   F   V   Q   D   R   H   R   A   R   N   R   L   R   K   D 819            828            837            846            855            864
CAA CTT AAG AAA CTT CCT GTA CAT AAA TTC AAG AAA GGA GAT GAG TAT GAT GTA
 Q   L   K   K   L   P   V   H   K   F   K   K   G   D   E   Y   D   V 873            882            891            900            909            918
TGT GCC ATT TGT TTG GAT GAG TAT GAA GAT GGA GAC AAA CTC AGA ATC CTT CCC
 C   A   I   C   L   D   E   Y   E   D   G   D   K   L   R   I   L   P 927            936            945            954            963            972
TGT TCC CAT GCT TAT CAT TGC AAG TGT GTA GAC CCT TGG CTA ACT AAA ACC AAA
 C   S   H   A   Y   H   C   K   C   V   D   P   W   L   T   K   T   K 981            990            999           1008           1017           1026
AAA ACC TGT CCA GTG TGC AAG CAA AAA GTT GTT CCT TCT CAA GGC GAT TCA GAC
 K   T   C   P   V   C   K   Q   K   V   V   P   S   Q   G   D   S   D 1035           1044           1053           1062           1071           1080
TCT GAC ACA GAC AGT AGT CAA GAA AAT GAA GTG ACA GAA CAT ACC CCT TTA
 S   D   T   D   S   S   Q   E   E   N   E   V   T   E   H   T   P   L 1089           1098           1107           1116           1125           1134
CTG AGA CCT TTA GCT TCT GTC AGT GCC CAG TCA TTT GGG GCT TTA TCG GAA TCC
 L   R   P   L   A   S   V   S   A   Q   S   F   G   A   L   S   E   S
```

FIGURE 1C

```
     1143           1152           1161           1170           1179           1188
CGC TCA CAT    CAG AAC ATG    ACA GAA TCT    TCA GAC TAT    GAG GAA GAC    GAC AAT GAA
 R   S   H      Q   N   M      T   E   S      S   D   Y      E   E   D      D   N   E 1197           1206           1215           1224           1233           1242
GAT ACT GAC    AGT AGT GAT    GCA GAA AAT    GAA ATT AAT    GAA CAT GAT    GTC GTG GTC
 D   T   D      S   S   D      A   E   N      E   I   N      E   H   D      V   V   V 1251           1260           1269           1278           1287           1296
CAG TTG CAG    CCT AAT GGT    GAA CGG GAT    TAC AAC ATA    GCA AAT ACT    GTT TGA CTT
 Q   L   Q      P   N   G      E   R   D      Y   N   I      A   N   T      V   *

1305           1314           1323           1332           1341           1350
TCA GAA GAT    GAT TGG TTT    ATT TCC CTT    TAA AAT GAT    TAG GTA TAT    ACT GTA ATT 1359           1368           1377           1386           1395           1404
TGA TTT TTT    GCT CCC TTC    AAA GAT TTC    TGT AGA AAT    AAC TTA TTT    TTT AGT ATT 1413           1422           1431           1440           1449           1458
CTA CAG TTT    AAT CAA ATT    ACT GAA ACA    GGA CTT TTG    ATC TGG TAT    TTA TCT GCC 1467           1476           1485           1494           1503           1512
AAG AAT ATA    CTT CAT TCA    CTA ATA ATA    GAC TGG TGC    TGT AAC TCA    AGC ATC AAT
```

FIGURE 1D

```
        1521        1530                           1539
        TCA GCT CTT CTT TTG GAA TGA AAG TAT AGC CA 3'
```

ZINC RING PROTEIN

This application is a divisional application of U.S. application Ser. No. 08/867,057, filed Jun. 2, 1997 now U.S. Pat. No. 5,840,555.

FIELD OF THE INVENTION

This invention relates to nucleic acid and amino acid sequences of a new human zinc RING protein and to the use of these sequences in the diagnosis, prevention, and treatment of inflammation and disorders associated with cell proliferation and apoptosis.

BACKGROUND OF THE INVENTION

Zinc binding (ZB) domains are found in numerous proteins which are involved in protein-nucleic acid or protein-protein interactions. ZB proteins are commonly involved in the regulation of gene expression, and may serve as transcription factors and signal transduction molecules. A ZB domain is generally composed of 25 to 30 amino acid residues which form one or more tetrahedral ion binding sites. The binding sites contain four ligands consisting of the sidechains of cysteine, histidine and occasionally aspartate or glutamate. The binding of zinc allows relatively short stretches of polypeptide to fold into defined structural units which are well-suited to participate in macromolecular interactions (Berg, J. M. et al. (1996) Science 271: 1081–1085).

Classes of ZB domains are characterized according to the number and positions of the residues involved in the zinc atom coordination. ZB domains which contain a $C_3HC_4$ sequence motif are known as RING domains (Lovering, R. et al. (1993) Proc. Natl. Acad. Sci. 90: 2112–2116). The RING domain binds two zinc ions in an arrangement structurally different from that of the zinc finger. The RING domain consists of eight metal binding residues, and the sequences that bind the two metal ions overlap (Barlow, P. N. et al. (1994) J. Mol. Biol. 237: 201–211). The consensus sequence $C-X_2-C-X_{(9-27)}-C-X_{(1-3)}-H-X_{(2-3)}-C-X_2-C-X_{(4-48)}-C-X_2-C$ provides for loops of varying length which form the overlapping Zn binding sites. The two Zn binding sites are formed by four pairs of metal-binding Cys and His residues. The first and third pairs bind one metal ion, while the second and fourth pairs bind the other (Barlow, et al., supra). Functions of RING finger proteins are mediated through DNA binding and include the regulation of gene expression, DNA recombination, and DNA repair.

The murine BMI-1 gene encodes a protein of 324 amino acids. This protein, which is found in the nuclei of a variety of normal cells, contains a RING domain near the amino-terminus (Haupt, Y. et al. (1991) Cell 65: 753–763). Retroviral insertional mutagenesis of E-mu/myc transgenic mice by infection with Moloney murine leukemia virus (MuLV) accelerates development of B lymphoid tumors. In about half of independently induced pre-B-cell lymphomas, the provirus integrates in or near the BMI-1 gene and causes enhanced transcription of BMI-1. Haupt et al. (supra) concluded that myc-induced lymphomagenesis may entail the concerted action of several genes including the putative nuclear regulator BMI-1.

The human BMI-1 gene encodes a protein of 326 amino acids which shares 98% identity to the mouse amino acid sequence (Alkema, M. J. et al. (1993) Hum. Mol. Genet. 2: 1597–1603). Fluorescence in situ hybridization (FISH) on metaphase chromosome spreads localized the human BMI-1 proto-oncogene to the short arm of chromosome 10 (10p13), a region known to show translocations and to be involved in various leukemias (Alkema et al., supra).

The breast and ovarian cancer susceptibility-1 (BRCA1) gene encodes a predicted protein of 1,863 amino acids which contains a RING domain in its amino-terminal region (Miki, Y. et al. (1994) Science 266: 66–71). BRCA1 is expressed in numerous tissues including breast and ovary. In sporadic breast cancer, BRCA1 mRNA levels are markedly decreased during the transition from carcinoma in situ to invasive cancer (Thompson M. E. et al. (1995) Nature Genet. 9: 444–450). Furthermore, experimental inhibition of BRCA1 expression with antisense oligonucleotides produced accelerated growth of normal and malignant mammary cells but had no effect on nonmammary epithelial cells. Thompson et al. (supra) suggest that BRCA1 may normally serve as a negative regulator of mammary epithelial cell growth and that this function is compromised in breast cancer either by direct mutation or by alterations in gene expression.

The chicken zinc RING protein, C-RZF, is 381 amino acids in length. Its expression occurs as a consequence of the binding of cytotactin/tenascin (CT/TN), a substrate adhesion molecule, to chicken embryo brain cells (Tranque, P. et al. (1996) Proc. Natl. Acad. Sci. 93: 3105–3109). In addition to the RING zinc-binding motif, C-RZF also contains a leucine zipper, a nuclear localization signal, and an acidic transcription activation domain. These results suggest that C-RZF binds DNA and functions as a transcription regulator in response to a signal transduction network related to the CT/TN expression. Alternatively, C-RZF may function in communication between cell adhesion events at the cell membrane and changes in the nucleus, which regulates cell shape, migration, or differentiation (Tranque et al., supra).

The discovery of a new human zinc RING protein and the polynucleotides encoding it satisfies a need in the art by providing new compositions which are useful in the diagnosis, prevention and treatment of inflammation and disorders associated with cell proliferation and apoptosis.

SUMMARY OF THE INVENTION

The invention features a substantially purified polypeptide, human zinc RING (ZIRI), having the amino acid sequence shown in SEQ ID NO:1, or fragments thereof.

The invention further provides an isolated and substantially purified polynucleotide sequence encoding the polypeptide comprising the amino acid sequence of SEQ ID NO:1 or fragments thereof. In a particular aspect, the polynucleotide is the nucleotide sequence of SEQ ID NO:2 or variants thereof.

In addition, the invention provides a polynucleotide sequence which hybridizes under stringent conditions to the polynucleotide sequence of SEQ ID NO:2. In another aspect the invention provides a composition comprising an isolated and purified polynucleotide sequence encoding ZIRI.

The invention further provides a polynucleotide sequence comprising the complement of the polynucleotide sequence encoding the amino acid sequence of SEQ ID NO:1, or fragments or variants thereof. In a particular aspect, the polynucleotide sequence is the complement of SEQ ID NO:2. In another aspect the invention provides a composition comprising an isolated and purified polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1 or a fragment thereof, the method comprising the steps of: a) culturing the host cell containing an expression vector containing at least a fragment of the polynucleotide sequence encoding ZIRI under conditions suitable for the expression of the polypeptide; and b) recovering the polypeptide from the host cell culture.

The invention also provides a pharmaceutical composition comprising a substantially purified ZIRI having the amino acid sequence of SEQ ID NO:1 in conjunction with a suitable pharmaceutical carrier.

The invention also provides a purified antagonist which decreases the activity of a polypeptide of SEQ ID NO:1. In one aspect the invention provides a purified antibody which binds to a polypeptide comprising at least a fragment of the amino acid sequence of SEQ ID NO:1.

Still further, the invention provides a purified agonist which modulates the activity of the polypeptide of SEQ ID NO:1.

The invention features methods for treating or preventing inflammation or cancer by administering an antagonist of ZIRI. The invention also features methods for treating or preventing a disorder associated with apoptosis or for stimulating cell proliferation by administering ZIRI.

The invention also provides a method for detecting a polynucleotide which encodes ZIRI in a biological sample comprising the steps of: a) hybridizing a polynucleotide sequence complementary to ZIRI (SEQ ID NO:1) to nucleic acid material of a biological sample, thereby forming a hybridization complex; and b) detecting the hybridization complex, wherein the presence of the complex correlates with the presence of a polynucleotide encoding ZIRI in the biological sample. In a preferred embodiment, prior to hybridization, the nucleic acid material of the biological sample is amplified by the polymerase chain reaction.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of ZIRI. The alignment was produced using MACDNASIS PRO™ software (Hitachi Software Engineering Co. Ltd. San Bruno, Calif.).

FIGS. 2A and 2B show the amino acid sequence alignments between ZIRI (SEQ ID NO:1) and a chicken zinc RING protein, C-RZF (GI 1321818; SEQ ID NO:3), produced using the multisequence alignment program of DNASTAR™ software (DNASTAR Inc, Madison Wis.).

DESCRIPTION OF THE INVENTION

Figure 3A:
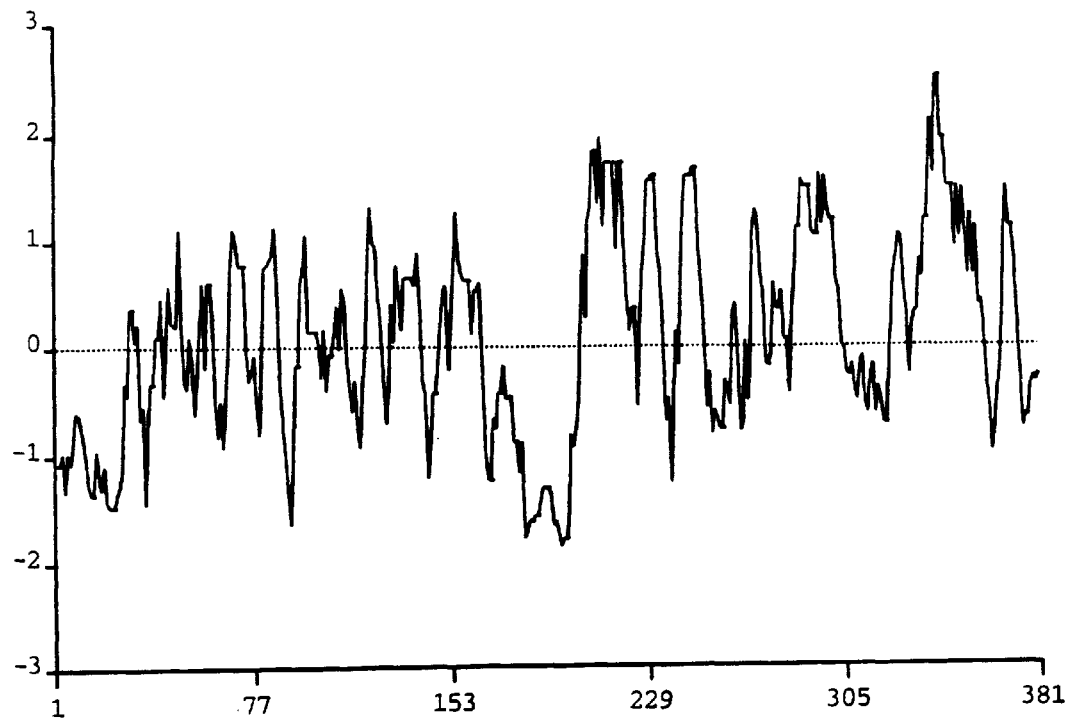
FIGS. 3A and 3B show the hydrophobicity plots for ZIRI, SEQ ID NO:1 and C-RZF (SEQ ID NO:3), respectively. The positive X axis reflects amino acid position, and the negative Y axis, hydrophobicity (MACDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

ZIRI, as used herein, refers to the amino acid sequences of substantially purified ZIRI obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to ZIRI, increases or prolongs the duration of the effect of ZIRI. Agonists may include proteins, nucleic acids, carbohydrates, or any other molecules which bind to and modulate the effect of ZIRI.

An "allele" or "allelic sequence", as used herein, is an alternative form of the gene encoding ZIRI. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding ZIRI, as used herein, include those with deletions, insertions, or substitutions of different nucleotides resulting in a polynucleotide that encodes the same or a functionally equivalent ZIRI. Included within this definition are polymorphisms which may or may not be readily detectable using a particular oligonucleotide probe of the polynucleotide encoding ZIRI, and improper or unexpected hybridization to alleles, with a locus other than the normal chromosomal locus for the polynucleotide sequence encoding ZIRI. The encoded protein may also be "altered" and contain deletions, insertions, or substitutions of amino acid residues which produce a silent change and result in a fuctionally equivalent ZIRI. Deliberate amino acid substitutions may be made on the basis of similarity in polarity, charge, solubility, hydrophobicity, hydrophilicity, and/or the amphipathic nature of the residues as long as the biological or immunological activity of ZIRI is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence", as used herein, refers to an oligopeptide, peptide, polypeptide, or protein sequence, and fragment thereof, and to naturally occurring or synthetic molecules. Fragments of ZIRI are preferably about 5 to about 15 amino acids in length and retain the biological activity or the immunological activity of ZIRI. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification", as used herein, refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist", as used herein, refers to a molecule which, when bound to ZIRI, decreases the amount or the duration of the effect of the biological or immunological activity of ZIRI. Antagonists may include proteins, nucleic acids, carbohydrates, or any other molecules which decrease the effect of ZIRI.

As used herein, the term "antibody" refers to intact molecules as well as fragments thereof, such as Fa, F(ab')$_2$, and Fv, which are capable of binding the epitopic determinant. Antibodies that bind ZIRI polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic ZIRI, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by basepairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence", as used herein, refers broadly to any composition containing the given polynucleotide sequence. The composition may comprise a dry formulation or an aqueous solution. Compositions comprising polynucleotide sequences encoding ZIRI (SEQ ID NO:1) or fragments thereof (e.g., SEQ ID NO:2 and fragments thereof) may be employed as hybridization probes. The probes may be stored in freezedried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2 by northern analysis is indicative of the presence of mRNA encoding ZIRI in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to ZIRI or the encoded ZIRI. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15: 345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to a high-density array of distinct polynucleotides or oligonucleotides synthesized on a substrate, such as paper, nylon or other type of membrane, filter, chip, glass slide, or any other suitable solid support.

The term "modulate", as used herein, refers to a change in the activity of ZIRI. For example, modulation may cause an increase or a decrease in protein activity, binding characteristics, or any other biological, functional or immunological properties of ZIRI.

"Nucleic acid sequence", as used herein, refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or hybridization assays. As used herein, oligonucleotide is substantially equivalent to the terms "amplimers", "primers", "oligomers", and "probes", as commonly defined in the art.

"Peptide nucleic acid", PNA, as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8: 53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of SEQ ID NO:1" encompasses the full-length ZIRI and fragments thereof.

The term "sample", as used herein, is used in its broadest sense. A biological sample suspected of containing nucleic acid encoding ZIRI, or fragments thereof, or ZIRI itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

The terms "specific binding" or "specifically binding", as used herein, refer to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of ZIRI, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human zinc RING protein (hereinafter referred to as "ZIRI"), the polynucleotides encoding ZIRI, and the use of these compositions for the diagnosis, prevention, or treatment of inflammation and disorders associated with cell proliferation and apoptosis.

Nucleic acids encoding ZIRI of the present invention were first identified in Incyte Clone 104119 from the bone marrow cDNA library (BMARNOT02) using a computer search for amino acid sequence alignments. A consensus sequence, SEQ ID NO:2, was derived from the following overlapping and/or extended nucleic acid sequences: Incyte Clones 2453340 (ENDANOT01), 175010 (TLYMNOT01), and 104119 (BMARNOT02).

Figure 3B:
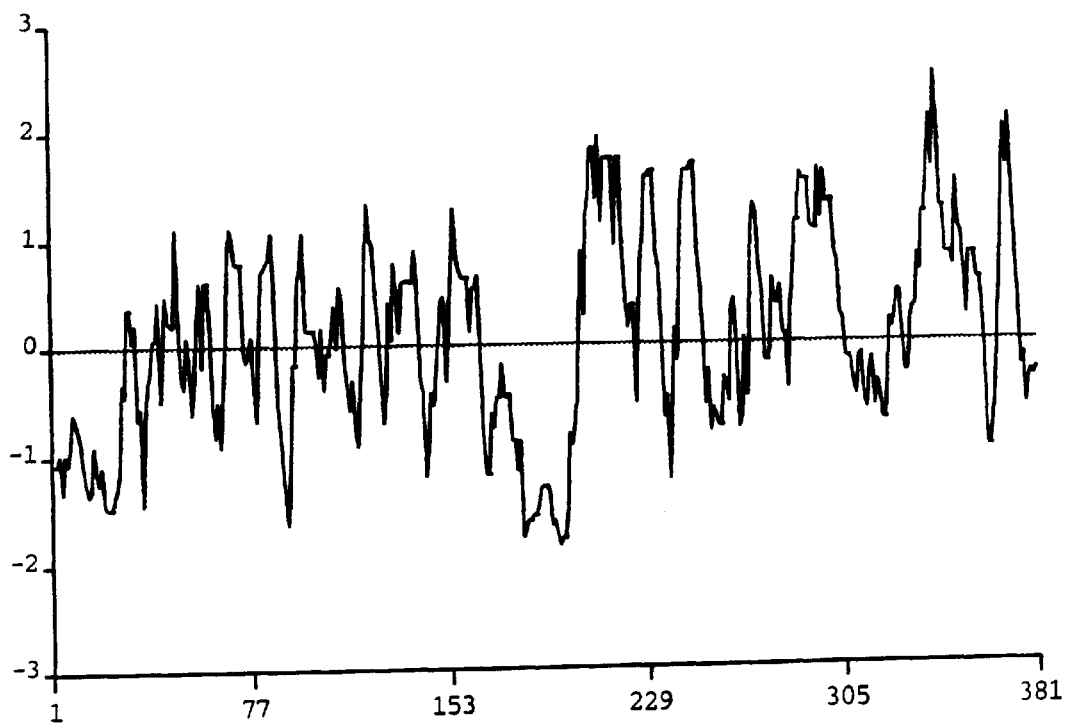

In one embodiment, the invention encompasses a polypeptide comprising the amino acid sequence of SEQ ID NO:1, as shown in FIGS. 1A, 1B, 1C, 1D and 1E. ZIRI is 381 amino acids in length. It has a zinc RING motif encompassing residues C240–C281 which has the C3HC4 RING signature. In addition, ZIRI has a leucine zipper motif encompassing residues L13-G56, a nuclear localization signal motif encompassing residues R210 and K220, and an acidic transcription activation domain encompassing residues D291–D361. These conserved motifs are essential for the functions of ZIRI in binding DNA, regulating cell adhesion signals between the cell membrane and nucleus, and host defense. ZIRI also has three potential N-glycosylation sites at N43, N88, and N334, ten potential casein kinase II phosphorylation sites encompassing residues T47-D50, S71-E74, S157-D160, S288-D191, S292-D295, S294-D297, S298-E301, S299-E302, S339-E342, and S352-E355, and three potential protein kinase C phosphorylation sites encompassing S157-K159 and T274-K276. As shown in FIGS. 2A and 2B, ZIRI has chemical and structural homology with a zinc RING protein, C-RZF (GI 1321818; SEQ ID NO:3). In particular, ZIRI and C-RZF share 91% identity. As illustrated by FIGS. 3A and 3B, ZIRI and C-RZF have rather similar hydrophobicity plots. Northern analysis shows the expression of this sequence in various cDNA libraries, at least 51% of which are immortalized or cancerous, at least 14% of which involve immune response, and at least 14% of which involve infant/fetal tissues or organs.

The invention also encompasses ZIRI variants. A preferred ZIRI variant is one having at least 80%, and more preferably 90%, amino acid sequence identity to the ZIRI amino acid sequence (SEQ ID NO:1). A most preferred ZIRI variant is one having at least 95% amino acid sequence identity to SEQ ID NO:1.

The invention also encompasses polynucleotides which encode ZIRI. Accordingly, any nucleic acid sequence which encodes the amino acid sequence of ZIRI can be used to produce recombinant molecules which express ZIRI. In a particular embodiment, the invention encompasses the polynucleotide comprising the nucleic acid sequence of SEQ ID NO:2 as shown in FIGS. 1A, 1B, 1C, 1D and 1E.

It will be appreciated by those skilled in the art that as a result of the degeneracy of the genetic code, a multitude of nucleotide sequences encoding ZIRI, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring ZIRI, and all such variations are to be considered as being specifically disclosed.

Although nucleotide sequences which encode ZIRI and its variants are preferably capable of hybridizing to the nucleotide sequence of the naturally occurring ZIRI under appropriately selected conditions of stringency, it may be advantageous to produce nucleotide sequences encoding ZIRI or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding ZIRI and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode ZIRI and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding ZIRI or any fragment thereof.

Also encompassed by the invention are polynucleotide sequences that are capable of hybridizing to the claimed nucleotide sequences, and in particular, those shown in SEQ ID NO:2, under various conditions of stringency as taught in Wahl, G. M. and S. L. Berger (1987; Methods Enzymol. 152: 399–407) and Kimmel, A. R. (1987; Methods Enzymol. 152: 507–511).

Methods for DNA sequencing which are well known and generally available in the art and may be used to practice any of the embodiments of the invention. The methods may employ such enzymes as the Klenow fragment of DNA polymerase I, SEQUENASE® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; M J Research, Watertown, Mass.) and the ABI Catalyst and 373 and 377 DNA Sequencers (Perkin Elmer).

The nucleic acid sequences encoding ZIRI may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2: 318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16: 8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1: 111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19: 3055–3060). Additionally, one may use PCR, nested primers, and PROMOTERFINDER™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER™ and SEQUENCE NAVIGATOR™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode ZIRI may be used in recombinant DNA molecules to direct expression of ZIRI, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express ZIRI.

As will be understood by those of skill in the art, it may be advantageous to produce ZIRI-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter ZIRI encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding ZIRI may be ligated to a heterologous sequence to encode a fusion protein. For example, to screen peptide libraries for inhibitors of ZIRI activity, it may be useful to encode a chimeric ZIRI protein that can be recognized by a commercially available antibody. A fusion protein may also be engineered to contain a cleavage site located between the ZIRI encoding sequence and the heterologous protein sequence, so that ZIRI may be cleaved and purified away from the heterologous moiety.

In another embodiment, sequences encoding ZIRI may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of ZIRI, or a fragment thereof For example, peptide synthesis can be performed using various solid-phase techniques (Roberge, J. Y. et al. (1995) Science 269: 202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles,* W H Freeman and Co., New York, N.Y.). The composition of the synthetic peptides may be confirmed by amino acid analysis or sequencing (e.g., the Edman degradation procedure; Creighton, supra). Additionally, the amino acid sequence of ZIRI, or any part thereof, may be altered during direct synthesis and/or combined using chemical methods with sequences from other proteins, or any part thereof, to produce a variant polypeptide.

In order to express a biologically active ZIRI, the nucleotide sequences encoding ZIRI or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding ZIRI and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding ZIRI. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla, Calif.) or PSPORT1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding ZIRI, vectors based on SV40 or EBV may be used with an appropriate selectable marker.

In bacterial systems, a number of expression vectors may be selected depending upon the use intended for ZIRI. For example, when large quantities of ZIRI are needed for the induction of antibodies, vectors which direct high level expression of fusion proteins that are readily purified may be used. Such vectors include, but are not limited to, the multifunctional *E. coli* cloning and expression vectors such as BLUESCRIPT® (Stratagene), in which the sequence encoding ZIRI may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264: 5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153: 516–544.

In cases where plant expression vectors are used, the expression of sequences encoding ZIRI may be driven by any of a number of promoters. For example, viral promoters such as the 35S and 19S promoters of CaMV may be used alone or in combination with the omega leader sequence from TMV (Takamatsu, N. (1987) EMBO J. 6: 307–311). Alternatively, plant promoters such as the small subunit of RUBISCO or heat shock promoters may be used (Coruzzi, G. et al. (1984) EMBO J. 3: 1671–1680; Broglie, R. et al. (1984) Science 224: 838–843; and Winter, J. et al. (1991) Results Probl. Cell Differ. 17: 85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express ZIRI. For example, in one such system, *Autographa californica* nuclear polyhedrosis virus (AcNPV) is used as a vector to express foreign genes in *Spodoptera frugiperda* cells or in Trichoplusia larvae. The sequences encoding ZIRI may be cloned into a non-essential region of the virus, such as the polyhedrin gene, and placed under control of the polyhedrin promoter. Successful insertion of ZIRI will render the polyhedrin gene inactive and produce recombinant virus lacking coat protein. The recombinant viruses may then be used to infect, for example, *S. frugiperda* cells or Trichopulsia larvae in which ZIRI may be expressed (Engelhard, E. K. et al. (1994) Proc. Nat. Acad. Sci. 91: 3224–3227).

In mammalian host cells, a number of viral-based expression systems may be utilized. In cases where an adenovirus is used as an expression vector, sequences encoding ZIRI may be ligated into an adenovirus transcription/translation complex consisting of the late promoter and tripartite leader sequence. Insertion in a non-essential E1 or E3 region of the viral genome may be used to obtain a viable virus which is capable of expressing ZIRI in infected host cells (Logan, J. and Shenk, T. (1984) Proc. Natl. Acad. Sci. 81: 3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding ZIRI. Such signals include the ATG initiation codon and adjacent sequences. In cases where sequences encoding ZIRI, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20: 125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express ZIRI may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11: 223–32) and adenine phosphoribosyltransferase (Lowy, I. et al. (1980) Cell 22: 817–23) genes which can be employed in $tk^-$ or $aprt^-$ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77: 3567–70); npt, which confers resistance to the aminoglycosides neomycin and G-418 (Colbere-Garapin, F. et al (1981) J. Mol. Biol. 150: 1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85: 8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55: 121–131).

Although the presence/absence of marker gene expression suggests that the gene of interest is also present, its presence and expression may need to be confirmed. For example, if the sequence encoding ZIRI is inserted within a marker gene sequence, transformed cells containing sequences encoding ZIRI can be identified by the absence of marker gene function. Alternatively, a marker gene can be placed in tandem with a sequence encoding ZIRI under the control of a single promoter. Expression of the marker gene in response to induction or selection usually indicates expression of the tandem gene as well.

Alternatively, host cells which contain the nucleic acid sequence encoding ZIRI and express ZIRI may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding ZIRI can be detected by DNA-DNA or DNA-RNA hybridization or amplification using probes or fragments or fragments of polynucleotides encoding ZIRI. Nucleic acid amplification based assays involve the use of oligonucleotides or oligomers based on the sequences encoding ZIRI to detect transformants containing DNA or RNA encoding ZIRI.

A variety of protocols for detecting and measuring the expression of ZIRI, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on ZIRI is preferred, but a competitive binding assay may be employed. These and other assays are described, among other places, in Hampton, R. et al. (1990; *Serological Methods, a Laboratory Manual,* APS Press, St Paul, Minn.) and Maddox, D. E. et al. (1983; J. Exp. Med. 158: 1211–1216).

A wide variety of labels and conjugation techniques are known by those skilled in the art and may be used in various nucleic acid and amino acid assays. Means for producing labeled hybridization or PCR probes for detecting sequences related to polynucleotides encoding ZIRI include oligolabeling, nick translation, end-labeling or PCR amplification using a labeled nucleotide. Alternatively, the sequences encoding ZIRI, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding ZIRI may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode ZIRI may be designed to contain signal sequences which direct secretion of ZIRI through a prokaryotic or eukaryotic cell membrane. Other constructions may be used to join sequences encoding ZIRI to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and ZIRI may be used to facilitate purification. One such expression vector provides for expression of a fusion protein containing ZIRI and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif. 3: 263–281) while the enterokinase cleavage site provides a means for purifying ZIRI from the fusion protein. A discussion of vectors which contain fusion proteins is provided in Kroll, D. J. et al. (1993; DNA Cell Biol. 12: 441–453).

In addition to recombinant production, fragments of ZIRI may be produced by direct peptide synthesis using solid-phase techniques Merrifield J. (1963) J. Am. Chem. Soc. 85: 2149–2154). Protein synthesis may be performed using manual techniques or by automation. Automated synthesis may be achieved, for example, using Applied Biosystems 431A Peptide Synthesizer (Perkin Elmer). Various fragments of ZIRI may be chemically synthesized separately and combined using chemical methods to produce the full length molecule.

Therapeutics

Chemical and structural homology exists between ZIRI and a chicken zinc RING protein, C-RZF (GI 1321818). Northern analysis shows that the expression of ZIRI is associated with cell proliferation, inflammation, fetal and infant development, and immune response.

During fetal development, decreased expression of ZIRI may result in increased apoptosis with no adverse effects. However, in other situations such as in adults, decreased expression of ZIRI may cause an increase in apoptosis which is associated with several disorders in which apoptosis is detrimental to the subject. Therefore, in one embodiment, ZIRI or a fragment or derivative thereof may be administered to a subject to prevent or treat a disorder associated with apoptosis. Such disorders include, but are not limited to, AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as by hepatitis B and C, and osteoporosis.

In another embodiment, an agonist which is specific for ZIRI may be used to prevent or treat a disorder associated with increased apoptosis including, but not limited to, those listed above.

In still another embodiment, a vector capable of expressing ZIRI, or a fragment or a derivative thereof, may be used to prevent or treat a disorder associated with increased apoptosis including, but not limited to, those listed above.

In a further embodiment, ZIRI or a fragment or derivative thereof may be added to cells to stimulate cell proliferation. In particular, ZIRI may be added to a cell or cells in vivo using delivery mechanisms such as liposomes, viral based vectors, or electroinjection for the purpose of promoting regeneration or cell differentiation of the cell or cells. In addition, ZIRI may be added to a cell, cell line, tissue or organ culture in vitro or ex vivo to stimulate cell proliferation for use in heterologous or autologous transplantation. In some cases, the cell will have been selected for its ability to fight an infection or a cancer or to correct a genetic defect in a disease such as sickle cell anemia, β thalassemia, cystic fibrosis, or Huntington's chorea.

In another further embodiment, an agonist which is specific for ZIRI may be administered to a cell to stimulate cell proliferation, as described above.

In another further embodiment, a vector capable of expressing ZIRI, or a fragment or a derivative thereof, may be administered to a cell or cells in vivo using delivery mechanisms, or to a cell to stimulate cell proliferation, as described above.

Increased expression of ZIRI appears to be associated with increased cell proliferation. Therefore, in one embodiment, an antagonist or an inhibitor of ZIRI, or a fragment or a derivative thereof, may be administered to a subject to prevent or treat a disorder associated with cell proliferation. Such disorders include various types of cancer including, but not limited to, adenocarcinoma, leukemia, lymphoma, melanoma, myeloma, sarcoma, and teratocarcinoma, and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for ZIRI may be used directly as an antagonist, or indirectly as a targeting or delivery mechanism for bringing a pharmaceutical agent to cells or tissue which express ZIRI.

In still another embodiment, a vector expressing the complementary sequence or antisense of the polynucleotide encoding ZIRI, or a fragment or a derivative thereof, may be administered to a subject to prevent or treat a disorder associated with cell proliferation including, but not limited to, those listed above.

In a further embodiment, an antagonist or an inhibitor of ZIRI or a fragment or a derivative thereof, may be administered to a subject to prevent or treat inflammation of any type and, in particular, that which results from a particular disorder. Such disorders with associated inflammation include, but are not limited to, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflamation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma. In one aspect, an antibody specific for ZIRI may be used directly as an antagonist, or indirectly as a targeting or delivery mechanism for bringing a pharmaceutical agent to cells or tissue which express ZIRI.

In another further embodiment, a vector expressing the complementary sequence or antisense of the polynucleotide encoding ZIRI, or a fragment or a derivative thereof, may be administered to a subject to prevent or treat inflammation of any type including, but not limited to, those listed above.

In other embodiments, any of the therapeutic proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

Antagonists or inhibitors of ZIRI may be produced using methods which are generally known in the art. In particular, purified ZIRI may be used to produce antibodies or to screen libraries of pharmaceutical agents to identify those which specifically bind ZIRI.

Antibodies to ZIRI may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with ZIRI or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to ZIRI have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of ZIRI amino acids may be fused with those of another protein such as keyhole limpet hemocyanin and antibody produced against the chimeric molecule.

Monoclonal antibodies to ZIRI may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256: 495–497; Kozbor, D. et al. (1985) J. Immunol. Methods 81: 31–42; Cote, R. J. et al. (1983) Proc. Natl. Acad. Sci. 80: 2026–2030; Cole, S. P. et al. (1984) Mol. Cell Biol. 62: 109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81: 6851–6855; Neuberger, M. S. et al. (1984) Nature 312: 604–608; Takeda, S. et al. (1985) Nature 314: 452–454). Alternatively, techniques described for the production of single chain antibodies may be adapted, using methods known in the art, to produce ZIRI-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88: 11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349: 293–299).

Antibody fragments which contain specific binding sites for ZIRI may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254: 1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between ZIRI and its specific antibody. A two-site, monoclonal-based immunoassay utilizing monoclonal antibodies reactive to two non-interfering ZIRI epitopes is preferred, but a competitive binding assay may also be employed (Maddox, supra).

In another embodiment of the invention, the polynucleotides encoding ZIRI, or any fragment or complement thereof, may be used for therapeutic purposes. In one aspect, the complement of the polynucleotide encoding ZIRI may be used in situations in which it would be desirable to block the transcription of the mRNA. In particular, cells may be transformed with sequences complementary to polynucleotides encoding ZIRI. Thus, complementary molecules or fragments may be used to modulate ZIRI activity, or to achieve regulation of gene function. Such technology is now well known in the art, and sense or antisense oligonucleotides or larger fragments, can be designed from various locations along the coding or control regions of sequences encoding ZIRI.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding ZIRI. These techniques are described both in Sambrook et al. (supra) and in Ausubel et al. (supra).

Genes encoding ZIRI can be turned off by transforming a cell or tissue with expression vectors which express high levels of a polynucleotide or fragment thereof which encodes ZIRI. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding ZIRI (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding ZIRI.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding ZIRI. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in virto, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15: 462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of ZIRI, antibodies to ZIRI, mimetics, agonists, antagonists, or inhibitors of ZIRI. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethylcellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of ZIRI, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example ZIRI or fragments thereof, antibodies of ZIRI, agonists, antagonists or inhibitors of ZIRI, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograns, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind ZIRI may be used for the diagnosis of conditions or diseases characterized by expression of ZIRI, or in assays to monitor patients being treated with ZIRI, agonists, antagonists or inhibitors. The antibodies useful for diagnostic purposes may be prepared in the same manner as those described above for therapeutics. Diagnostic assays for ZIRI include methods which utilize the antibody and a label to detect ZIRI in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring ZIRI are known in the art and provide a basis for diagnosing altered or abnormal levels of ZIRI expression. Normal or standard values for ZIRI expression are established by combining body fluids or cell extracts taken from normal mammalian subjects, preferably human, with antibody to ZIRI under conditions suitable for complex formation. The amount of standard complex formation may be quantified by various methods, but preferably by photometric means. Quantities of ZIRI expressed in subject samples, control and disease from biopsied tissues are compared with the standard values. Deviation between standard and subject values establishes the parameters for diagnosing disease.

In another embodiment of the invention, the polynucleotides encoding ZIRI may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of ZIRI may be correlated with disease. The diagnostic assay may be used to distinguish between absence, presence, and excess expression of ZIRI, and to monitor regulation of ZIRI levels during therapeutic intervention.

In one aspect, hybridization with PCR probes which are capable of detecting polynucleotide sequences, including genomic sequences, encoding ZIRI or closely related molecules, may be used to identify nucleic acid sequences which encode ZIRI. The specificity of the probe, whether it is made from a highly specific region, e.g., 10 unique nucleotides in the 5' regulatory region, or a less specific region, e.g., especially in the 3+ coding region, and the stringency of the hybridization or amplification (maximal, high, intermediate, or low) will determine whether the probe identifies only naturally occurring sequences encoding ZIRI, alleles, or related sequences.

Probes may also be used for the detection of related sequences, and should preferably contain at least 50% of the nucleotides from any of the ZIRI encoding sequences. The hybridization probes of the subject invention may be DNA or RNA and derived from the nucleotide sequence of SEQ ID NO:2 or from genomic sequence including promoter, enhancer elements, and introns of the naturally occurring ZIRI.

Means for producing specific hybridization probes for DNAs encoding ZIRI include the cloning of nucleic acid sequences encoding ZIRI or ZIRI derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding ZIRI may be used for the diagnosis of conditions, disorders, or diseases which are associated with expression of ZIRI. Examples of such disorders include: various types of cancer such as adenocarcinoma, leukemia, lymphoma, melanoma, myeloma, sarcoma, and teratocarcinoma, and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; disorders associated with inflammation such as Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; and disorders associated apoptosis such as AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as by hepatitis B and C, and osteoporosis. The polynucleotide sequences encoding ZIRI may be used in Southern or northern analysis, dot blot, or other membrane-based technologies; in PCR technologies; or in dipstick, pin, ELISA assays or microarrays utilizing fluids or tissues from patient biopsies to detect altered ZIRI expression. Such qualitative or quantitative methods are well known in the art.

In a particular aspect, the nucleotide sequences encoding ZIRI may be useful in assays that detect activation or induction of various cancers, particularly those mentioned above. The nucleotide sequences encoding ZIRI may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding ZIRI in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of ZIRI, a normal or standard profile for expression is established. This may be accomplished by combining body fluids or cell extracts taken from normal subjects, either animal or human, with a sequence, or a fragment thereof, which encodes ZIRI, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding ZIRI may involve the use of PCR. Such oligomers may be chemically synthesized, generated enzymatically, or produced in vitro. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of ZIRI include radiolabeling or biotinylating nucleotides, coamplification of a control nucleic acid, and standard curves onto which the experimental results are interpolated (Melby, P. C. et al. (1993) J. Immunol. Methods, 159: 235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or calorimetric response gives rapid quantitation.

In further embodiments, oligonucleotides derived from any of the polynucleotide sequences described herein may be used as probes in microarrays. The microarrays can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents.

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs fixed to a solid support. Microarrays may contain oligonucleotides which cover the known 5', or 3', sequence, or contain sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. The oligomers are synthesized at designated areas on a substrate using a light-directed chemical process. The substrate may be paper, nylon or other type of membrane, filter, chip, glass slide or any other suitable solid support.

In another aspect, the oligomers may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array may be produced by hand or using available devices (slot blot or dot blot apparatus) materials and machines (including robotic instruments) and contain grids of 8 dots, 24 dots, 96 dots, 384 dots, 1536 dots or 6144 dots, or any other multiple which lends itself to the efficient use of commercially available instrumentation.

In order to conduct sample analysis using the microarrays, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode ZIRI may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7: 127–134, and Trask, B. J. (1991) Trends Genet. 7: 149–154.

Fluorescent in situ hybridization (FISH as described in Verma et al. (1988) Human Chromosomes: A Manual of Basic Techniques, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding ZIRI on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336: 577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, ZIRI, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between ZIRI and the agent being tested, may be measured.

Another technique for drug screening which may be used provides for high throughput screening of compounds having suitable binding affinity to the protein of interest as described in published PCT application WO84/03564. In this method, as applied to ZIRI large numbers of different small test compounds are synthesized on a solid substrate, such as plastic pins or some other surface. The test compounds are reacted with ZIRI, or fragments thereof, and washed. Bound ZIRI is then detected by methods well known in the art. Purified ZIRI can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding ZIRI specifically compete with a test compound for binding ZIRI. In this manner, the antibodies can be used to detect the presence of any peptide which shares one or more antigenic determinants with ZIRI.

In additional embodiments, the nucleotide sequences which encode ZIRI may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I BMARNOT02 cDNA Library Construction

The BMARNOT02 cDNA library was constructed from a pooled sample of bone marrow from the breast bones of 24 males and females of Caucasian heritage whose ages ranged from 16 to 70 years.

The cDNA library was custom-constructed using this poly A RNA (Stratagene, La Jolla, Calif.). cDNA synthesis was primed using both oligo d(T) and random hexamers, and the two cDNA copies were treated separately. Synthetic adapter oligonucleotides were ligated onto cDNA ends enabling its insertion into the Stratagene UNI-ZAP™ vector system. Finally, the two cDNA libraries were combined into a single library by mixing equal numbers of bacteriophage.

The quality of the cDNA library was screened using DNA probes, and then, the pBLUESCRIPT® phagemid (Stratagene) was excised. Subsequently, the custom-constructed library phage particles were infected into E. coli host strain XLI-BLUE® (Stratagene). Alternative unidirectional vectors might include, but are not limited to, pcDNAI (Invitrogen, San Diego, Calif.) and pSHlox-1 (Novagen, Madison, Wis.).

II Isolation and Sequencing of cDNA Clones

The phagemid forms of individual cDNA clones were obtained by the in vivo excision process, in which the host bacterial strain was co-infected with both the library phage and an f1 helper phage. Polypeptides or enzymes derived from both the library-containing phage and the helper phage nicked the DNA, initiated new DNA synthesis from defined sequences on the target DNA, and created a smaller, single stranded circular phagemid DNA molecule that included all DNA sequences of the PBLUESCRIPT phagemid and the cDNA insert. The phagemid DNA was released from the cells and purified, and used to reinfect fresh host cells (SOLR, Stratagene) where double-stranded phagemid DNA was produced. Because the phagemid carries the gene for β-lactamase, the newly transformed bacteria were selected on medium containing ampicillin.

Phagemid DNA was also purified using the QIAWELL-8 Plasmid or QIAGEN® DNA Purification System (QIAGEN Inc, Chatsworth, Calif.). The DNA was eluted from the purification resin and prepared for DNA sequencing and other analytical manipulations.

An alternate method of purifying phagemid has recently become available. It utilizes the Miniprep Kit (Catalog No. 77468; GIBCO/BRL, Gaithersburg, Md.). This kit is in the 96-well format and provides enough reagents for 960 purifications. Each kit is provided with a recommended protocol, which has been employed except for the following changes. First, the 96 wells are each filled with only 1 ml of sterile terrific broth with carbenicillin at 25 mg/L and glycerol at 0.4%. After the wells are inoculated, the bacteria are cultured for 24 hours and lysed with 60 $\mu$l of lysis buffer. A centrifugation step (2900 rpm for 5 minutes) is performed before the contents of the block are added to the primary filter plate. The optional step of adding isopropanol to TRIS buffer is not routinely performed. After the last step in the protocol, samples are transferred to a Beckman 96-well block for storage.

The cDNA inserts from random isolates of the bone marrow cell library were sequenced in part. Methods for DNA sequencing are well known in the art. Conventional enzymatic methods employ DNA polymerase Klenow fragment, SEQUENASE™ (US Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-polyacrylamide gels and detected either by autoradiography (for radionuclide-labeled precursors) or by fluorescence (for fluorescent-labeled precursors). Recent improvements in mechanized reaction preparation, sequencing, and analysis such as those run on the Applied Biosystems 377 or 373 DNA sequencer and the Catalyst 800 use fluorescent detection methods.

III Homology Searching of cDNA Clones and Their Deduced Proteins

Using nucleotide sequences derived from the cDNA clones as query sequences (the sequences of the Sequence Listing), databases such as GenBank and EMBL which contain previously identified and annotated sequences are searched for areas of homology (similarity). Two homology search algorithms were used to identify sequences which are identical, nearly exact and definitely related.

The first algorithm was originally developed by Lipman D J and Pearson W R (1985 Science 227: 1435). In this algorithm, the homologous regions are searched in a two-step manner. In the first step, highly homologous regions are determined by calculating a matching score using a homology score table. In this step, the parameter "Ktup" is used to establish a shifting, minimum window size for comparing two sequences. Ktup also sets the number of bases that must match to extract the highest homologous region among the sequences. In this step, no insertions or deletions are applied, and the homology is displayed as an initial (INIT) value.

In the second step, the homologous regions are aligned to obtain the highest matching score by inserting a gap when it is needed to accommodate a probable deletion. The matching score obtained in the first step is recalculated using the homology score table and the insertion score table to produce an optimized value.

DNA homologies between two sequences may also be examined graphically using the Harr method of constructing dot matrix homology plots (Needleman, S. B. and Wunsch, C. O. (1970) J. Mol. Biol. 48: 443). This method produces a two-dimensional plot which can be useful in distinguishing between regions of homology and regions of repetition.

The second algorithm was developed by Applied Biosystems Inc and has been incorporated into the INHERIT™ 670 Sequence Analysis System. In this algorithm, Pattern Specification Language developed by TRW Inc (Los Angeles, Calif.) is used to determine regions of homology. INHERIT uses three parameters, window size, window offset, and error tolerance, in its sequence comparisons. Using a combination of these three parameters, the DNA database is searched for sequences containing regions of homology, and the appropriate sequences is scored with an initial value. Subsequently, these homologous regions are examined using dot matrix homology plots to regions of homology versus regions of repetition. Smith-Waterman alignments are used to display the results of the homology search.

Following the search for homologous nucleotide regions, the sequences from the cDNA clones were classified as to whether they are "exact" matches (approximately 97% of the determined sequence is identical to the reference sequence), homologous human matches (limited regions of significant similarity, but not exact matches), homologous non-human matches (limited regions of significant similarity with sequences from species other than human), or non-matches (no significant regions of homology to previously identified nucleotide sequences).

Searches of deduced polypeptides are analogous to those done with the cDNA sequences. The sequence of the polypeptide is used as a query sequence and compared to the previously identified sequences contained in a database such as Swiss/Prot or the NBRF Protein database. These polypeptides are initially scored for homology using a homology score table (Orcutt, B. C. and Dayhoff, M. O. (1995) Scoring Matrices, PIN Report MAT-0285) which results in an INIT score. The homologous regions are aligned to obtain the highest matching scores by inserting a gap which adds any probable deleted portion. The matching score is recalculated using the homology score table and the insertion score table resulting in an optimized score. In the absence of knowledge of proper reading frame, the polypeptide homology search may be performed in all three reading frames.

Peptide and polypeptide sequence homologies can also be ascertained using the INHERIT™ 670 Sequence Analysis System in an analogous manner to that used in DNA sequence analysis. Pattern Specification Language and parameter windows are used to search the polypeptide databases for sequences containing regions of homology and to assign an initial value. Subsequent examination with a dot-matrix homology plot distinguishes between regions of homology and regions of repetition.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as GenBank or the LIFESEQ™ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding ZIRI occurs. Abundance and percent abundance are also reported. Abundance directly reflects the number of times a particular transcript is represented in a cDNA library, and percent abundance is abundance divided by the total number of sequences examined in the cDNA library.

V Extension of ZIRI Encoding Polynucleotides

The nucleic acid sequence of the Incyte Clone 104119 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

| Step 1 | 94° C. for 1 min (initial denaturation) |
|---|---|
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQUICK™ (QIAGEN Inc., Chatsworth, Calif.), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2–3 hours or overnight at 16° C. Competent E. coli cells (in 40 μl of appropriate media) were transformed with 3 μl of ligation mixture and cultured in 80 μl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 μl of liquid LB/2× Carb medium placed in an individual well of an appropriate, commercially-available, sterile 96-well microtiter plate. The following day, 5 μl of each overnight culture was transferred into a non-sterile 96-well plate and after dilution 1:10 with water, 5 μl of each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
|---|---|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 μCi of [γ-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The canned images are examined to determine degree of complementarity and the relative bundance of each oligonucleotide sequence on the micro-array.

VIII Complementary Polynucleotides

Sequence complementary to the ZIRI-encoding sequence, or any part thereof, is used to decrease or inhibit expression of naturally occurring ZIRI. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of ZIRI, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the ZIRI-encoding transcript.

IX Expression of ZIRI

Expression of ZIRI is accomplished by subcloning the cDNAs into appropriate vectors and transforming the vectors into host cells. In this case, the cloning vector is also used to express ZIRI in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of ZIRI into the bacterial growth media which can be used directly in the following assay for activity.

X Demonstration of ZIRI Activity

ZIRI binding to DNA can be assessed by a method described by Zamore, P. et al. ((1992) Nature 355: 609–614). $^{32}$P-labeled DNA and ZIRI are incubated 1 hour at 25° C. with 20 unit RNasin, 1 mg/ml yeast TRNA in 50 mM KCl, 10 mM HEPES-KOH (pH 8.0), 0.025% Nonidet P-40, 1 mM dithiothreitol, and 10% glycerol. DNA-ZIRI complexes are then analyzed by electrophoresis on polyacrylamide gels.

XI Production of ZIRI Specific Antibodies

ZIRI that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring ZIRI Using Specific Antibodies

Naturally occurring or recombinant ZIRI is substantially purified by immunoaffinity chromatography using antibodies specific for ZIRI. An immunoaffinity column is constructed by covalently coupling ZIRI antibody to an activated chromatographic resin, such as CnBr-activated Sepharose (Pharmacia & Upjohn). After the coupling, the resin is blocked and washed according to the manufacturer's instructions.

Media containing ZIRI is passed over the immunoaffinity column, and the column is washed under conditions that allow the preferential absorbance of ZIRI (e.g., high ionic strength buffers in the presence of detergent). The column is eluted under conditions that disrupt antibody/ZIRI binding (eg, a buffer of pH 2–3 or a high concentration of a chaotrope, such as urea or thiocyanate ion), and ZIRI is collected.

XIII Identification of Molecules Which Interact with ZIRI

ZIRI or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled ZIRI, washed and any wells with labeled ZIRI complex are assayed. Data obtained using different concentrations of ZIRI are used to calculate values for the number, affinity, and association of ZIRI with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A substantially purified human zinc RING protein comprising the amino acid sequence of SEQ ID NO:1.

2. A pharmaceutical composition comprising a substantially purified human zinc RING protein having the amino acid sequence of SEQ ID NO:1 in conjunction with a suitable pharmaceutical carrier.

* * * * *

UNITED STATES PATENT AND TRADEMARK OFFICE
CERTIFICATE OF CORRECTION

PATENT NO. : 5,998,372  
DATED : December 7, 1999  
INVENTOR(S) : Hillman et al.

Page 1 of 1

It is certified that error appears in the above-identified patent and that said Letters Patent is hereby corrected as shown below:

<u>Title page,</u>  
Item [62], Related U.S. Application Data, please delete "[62] Division of application No. 08/867,057, Jun. 2, 1997, Pat. No. 5,840,555." and add  
-- [62] Division of application No. 08/867,057, June 2, 1997, Pat. No. 5,840,535. --

<u>Column 1,</u>  
Lines 4 and 5, please delete "Jun. 2, 1997 now U.S. Pat. No. 5,840,555." and add  
-- June 2, 1997 now U.S. Pat. No. 5,840,535. --

Signed and Sealed this

Sixth Day of August, 2002

*Attest:*

*Attesting Officer*

JAMES E. ROGAN  
*Director of the United States Patent and Trademark Office*

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 381 amino acids
      (B) TYPE: amino acid
      (C) STRANDEDNESS: single
      (D) TOPOLOGY: linear (vii) IMMEDIATE SOURCE:
      (A) LIBRARY: BMARNOT02
      (B) CLONE: 104119

(xi) SEQUENCE DESCRIPTION: SEQ ID NO:1:

```
Met Leu Leu Ser Ile Gly Met Leu Met Leu Ser Ala Thr Gln Val Tyr
 1               5                  10                  15

Thr Ile Leu Thr Val Gln Leu Phe Ala Phe Leu Asn Leu Leu Pro Val
                20                  25                  30

Glu Ala Asp Ile Leu Ala Tyr Asn Phe Glu Asn Ala Ser Gln Thr Phe
            35                  40                  45

Asp Asp Leu Pro Ala Arg Phe Gly Tyr Arg Leu Pro Ala Glu Gly Leu
    50                  55                  60

Lys Gly Phe Leu Ile Asn Ser Lys Pro Glu Asn Ala Cys Glu Pro Ile
65                  70                  75                  80

Val Pro Pro Val Lys Asp Asn Ser Ser Gly Thr Phe Ile Val Leu
                85                  90                  95

Ile Arg Arg Leu Asp Cys Asn Phe Asp Ile Lys Val Leu Asn Ala Gln
                100                 105                 110

Arg Ala Gly Tyr Lys Ala Ala Ile Val His Asn Val Asp Ser Asp Asp
            115                 120                 125

Leu Ile Ser Met Gly Ser Asn Asp Ile Glu Val Leu Lys Lys Ile Asp
    130                 135                 140

Ile Pro Ser Val Phe Ile Gly Glu Ser Ser Ala Asn Ser Leu Lys Asp
145                 150                 155                 160

Glu Phe Thr Tyr Glu Lys Gly Gly His Leu Ile Leu Val Pro Glu Phe
                165                 170                 175

Ser Leu Pro Leu Glu Tyr Tyr Leu Ile Pro Phe Leu Ile Ile Val Gly
            180                 185                 190

Ile Cys Leu Ile Leu Ile Val Ile Phe Met Ile Thr Lys Phe Val Gln
    195                 200                 205

Asp Arg His Arg Ala Arg Arg Asn Arg Leu Arg Lys Asp Gln Leu Lys
    210                 215                 220

Lys Leu Pro Val His Lys Phe Lys Lys Gly Asp Glu Tyr Asp Val Cys
225                 230                 235                 240

Ala Ile Cys Leu Asp Glu Tyr Glu Asp Gly Asp Lys Leu Arg Ile Leu
                245                 250                 255

Pro Cys Ser His Ala Tyr His Cys Lys Cys Val Asp Pro Trp Leu Thr
            260                 265                 270

Lys Thr Lys Lys Thr Cys Pro Val Cys Lys Gln Lys Val Val Pro Ser
    275                 280                 285

Gln Gly Asp Ser Asp Ser Asp Thr Asp Ser Ser Gln Glu Glu Asn Glu
    290                 295                 300

Val Thr Glu His Thr Pro Leu Leu Arg Pro Leu Ala Ser Val Ser Ala
```

```
305              310              315              320

Gln Ser Phe Gly Ala Leu Ser Glu Ser Arg Ser His Gln Asn Met Thr
                325              330              335

Glu Ser Ser Asp Tyr Glu Glu Asp Asp Asn Glu Asp Thr Asp Ser Ser
            340              345              350

Asp Ala Glu Asn Glu Ile Asn Glu His Asp Val Val Val Gln Leu Gln
        355              360              365

Pro Asn Gly Glu Arg Asp Tyr Asn Ile Ala Asn Thr Val
    370              375              380
```

(2) INFORMATION FOR SEQ ID NO:2:

(i) SEQUENCE CHARACTERISTICS:
        (A) LENGTH: 1544 base pairs
        (B) TYPE: nucleic acid
        (C) STRANDEDNESS: single
        (D) TOPOLOGY: linear (vii) IMMEDIATE SOURCE:
        (A) LIBRARY: BMARNOT02
        (B) CLONE: 104119

(xi) SEQUENCE DESCRIPTION: SEQ ID NO:2:

```
GTTGTCGTCC CTGCTAGTAC TCCGGGCTGT GGGGGTCGGT GCGGATATTC AGTCATGAAA      60

TCAGGGTAGG GACTTCTCCC GCAGCGACGC GGCTGGCAAG ACTGTTTGTG TTGCGGGGGC     120

CGGACTTCAA GGTGATTTTA CAACGAGATG CTGCTCTCCA TAGGGATGCT CATGCTGTCA     180

GCCACACAAG TCTACACCAT CTTGACTGTC CAGCTCTTTG CATTCTTAAA CCTACTGCCT     240

GTAGAAGCAG ACATTTTAGC ATATAACTTT GAAAATGCAT CTCAGACATT TGATGACCTC     300

CCTGCAAGAT TGGTTATAG ACTTCCAGCT GAAGGTTTAA AGGGTTTTTT GATTAACTCA      360

AAACCAGAGA ATGCCTGTGA ACCCATAGTG CCTCCACCAG TAAAAGACAA TTCATCTGGC     420

ACTTTCATCG TGTTAATTAG AAGACTTGAT TGTAATTTTG ATATAAAGGT TTTAAATGCA     480

CAGAGAGCAG GATACAAGGC AGCCATAGTT CACAATGTTG ATTCTGATGA CCTCATTAGC     540

ATGGGATCCA ACGACATTGA GGTACTAAAG AAAATTGACA TTCCATCTGT CTTTATTGGT     600

GAATCATCAG CTAATTCTCT GAAAGATGAA TTCACATATG AAAAGGGGG CCACCTTATC      660

TTAGTTCCAG AATTTAGTCT TCCTTTGGAA TACTACCTAA TTCCCTTCCT TATCATAGTG     720

GGCATCTGTC TCATCTTGAT AGTCATTTTC ATGATCACAA AATTTGTCCA GGATAGACAT     780

AGAGCTAGAA GAAACAGACT TCGTAAAGAT CAACTTAAGA AACTTCCTGT ACATAAATTC     840

AAGAAAGGAG ATGAGTATGA TGTATGTGCC ATTTGTTTGG ATGAGTATGA AGATGGAGAC     900

AAACTCAGAA TCCTTCCCTG TTCCCATGCT TATCATTGCA AGTGTGTAGA CCCTTGGCTA     960

ACTAAAACCA AAAAACCTG TCCAGTGTGC AAGCAAAAAG TTGTTCCTTC TCAAGGCGAT     1020

TCAGACTCTG ACACAGACAG TAGTCAAGAA GAAATGAAG TGACAGAACA TACCCCTTTA     1080

CTGAGACCTT TAGCTTCTGT CAGTGCCCAG TCATTTGGGG CTTTATCGGA ATCCCGCTCA    1140

CATCAGAACA TGACAGAATC TTCAGACTAT GAGGAAGACG ACAATGAAGA TACTGACAGT    1200

AGTGATGCAG AAAATGAAAT TAATGAACAT GATGTCGTGG TCCAGTTGCA GCCTAATGGT    1260

GAACGGGATT ACAACATAGC AAATACTGTT TGACTTTCAG AAGATGATTG GTTTATTTCC    1320

CTTTAAAATG ATTAGGTATA TACTGTAATT TGATTTTTTG CTCCCTTCAA AGATTTCTGT    1380

AGAAATAACT TATTTTTTAG TATTCTACAG TTTAATCAAA TTACTGAAAC AGGACTTTTG    1440

ATCTGGTATT TATCTGCCAA GAATATACTT CATTCACTAA TAATAGACTG GTGCTGTAAC    1500

TCAAGCATCA ATTCAGCTCT TCTTTTGGAA TGAAAGTATA GCCA                     1544
```

(2) INFORMATION FOR SEQ ID NO:3:

(i) SEQUENCE CHARACTERISTICS:
        (A) LENGTH: 381 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1321818

(xi) SEQUENCE DESCRIPTION: SEQ ID NO:3:

```
Met Leu Leu Ser Ile Gly Met Leu Met Leu Ser Ala Thr Gln Ile Tyr
  1               5                  10                  15

Thr Ile Val Thr Val Gln Leu Phe Ala Phe Leu Asn Leu Leu Pro Val
             20                  25                  30

Glu Ala Asp Ile Leu Ala Tyr Asn Phe Glu Asn Gly Thr Gln Thr Phe
         35                  40                  45

Asp Asp Leu Pro Ala Arg Phe Gly Tyr Arg Leu Pro Ala Glu Gly Leu
     50                  55                  60

Lys Gly Phe Leu Ile Asn Ser Lys Pro Glu Asn Ala Cys Glu Pro Ile
 65                  70                  75                  80

Ala Pro Pro Leu Arg Asp Asn Ser Thr Ala Phe Ile Val Leu
                 85                  90                  95

Ile Arg Arg Leu Glu Cys Asn Phe Asp Ile Lys Val Leu Asn Ala Gln
                100                 105                 110

Arg Ala Gly Tyr Lys Ala Ala Ile Val His Asn Val Asp Ser Asp Asp
            115                 120                 125

Leu Ile Ser Met Gly Ser Asn Asp Ile Glu Ile Leu Lys Lys Ile Asp
    130                 135                 140

Ile Pro Ser Val Phe Ile Gly Glu Ala Ser Ala Asn Ser Leu Lys Glu
145                 150                 155                 160

Glu Phe Thr Tyr Glu Lys Gly Gly His Val Val Leu Ile Pro Glu Phe
                165                 170                 175

Ser Leu Pro Leu Glu Tyr Tyr Leu Ile Pro Phe Leu Ile Ile Val Gly
            180                 185                 190

Ile Cys Leu Ile Leu Ile Val Ile Phe Met Ile Thr Lys Phe Val Gln
            195                 200                 205

Asp Arg His Arg Ala Arg Arg Asn Arg Leu Arg Lys Asp Gln Leu Lys
            210                 215                 220

Lys Leu Pro Val His Lys Phe Lys Lys Gly Asp Glu Tyr Asp Val Cys
225                 230                 235                 240

Ala Ile Cys Leu Asp Glu Tyr Glu Asp Gly Asp Lys Leu Arg Ile Leu
                245                 250                 255

Pro Cys Ser His Ala Tyr His Cys Lys Cys Val Asp Pro Trp Leu Thr
            260                 265                 270

Lys Thr Lys Lys Thr Cys Pro Val Cys Lys Gln Lys Val Val Pro Ser
    275                 280                 285

Gln Gly Asp Ser Asp Ser Glu Thr Asp Ser Ser Gln Glu Glu Asn Glu
            290                 295                 300

Val Ser Glu Asn Thr Pro Leu Leu Arg Pro Leu Ala Ser Val Ser Thr
305                 310                 315                 320

Gln Ser Phe Gly Ala Leu Ser Glu Ser His Ser His Gln Asn Met Thr
                325                 330                 335

Glu Ser Ser Glu Tyr Glu Glu Asp Asp Asn Asp Asn Ile Asp Ser Ser
```

-continued

```
            340                 345                 350
Asp Ala Glu Ser Gly Val Asn Glu Glu Ser Val Val Val Gln Leu Gln
        355                 360                 365

Pro Asn Asp Glu Arg Asp Tyr Arg Val Thr Asn Thr Val
    370                 375                 380
```